US006680054B1

(12) United States Patent
Reece et al.

(10) Patent No.: US 6,680,054 B1
(45) Date of Patent: Jan. 20, 2004

(54) MACROMOLECULAR NEURAMINIDASE-BINDING COMPOUNDS

(75) Inventors: Phillip A. Reece, Victoria (AU); Keith Geoffrey Watson, Victoria (AU); Wen-Yang Wu, Victoria (AU); Betty Jin, Victoria (AU); Guy Y. Krippner, Victoria (AU)

(73) Assignee: Biota Scientific Management PTY Ltd., Melborne (AU)

( * ) Notice: Subject to any disclaimer, the term of this patent is extended or adjusted under 35 U.S.C. 154(b) by 0 days.

(21) Appl. No.: 09/308,076

(22) PCT Filed: Nov. 13, 1997

(86) PCT No.: PCT/AU97/00771

§ 371 (c)(1),
(2), (4) Date: Jul. 14, 1999

(87) PCT Pub. No.: WO98/21243

PCT Pub. Date: May 22, 1998

(30) Foreign Application Priority Data

Nov. 14, 1996 (AU) .............................................. PO3632
Aug. 14, 1997 (AU) .............................................. PO8539

(51) Int. Cl.[7] ......................... A61K 39/44; A61K 31/35

(52) U.S. Cl. ........................ 424/181.1; 435/5; 514/459; 530/402

(58) Field of Search ............................. 514/459; 435/5; 424/181.1; 530/402

(56) References Cited

U.S. PATENT DOCUMENTS 5,221,611 A 6/1993 Stenglein et al. ............ 435/7.1
5,360,817 A 11/1994 Von Izstein et al. ........ 514/459
5,681,811 A 10/1997 Ekwuribe ...................... 514/8
6,548,476 B1 * 4/2003 Wu et al. ...................... 514/2

FOREIGN PATENT DOCUMENTS

| | | |
|---|---|---|
| AU | 706810 | 9/1997 |
| WO | WO 94/11005 | 11/1992 |
| WO | WO95/32712 | 12/1995 |
| WO | 97/06157 | 2/1997 |
| WO | WO 97/32214 | 2/1997 |
| WO | WO 98/03572 | 1/1998 |

OTHER PUBLICATIONS

Zalipsky, Functionalized Poly(ethylene glycol) for Preparation of Biologically Relevant Conjugates. Bioconjugate Chemistry 6:150–165, 1995.

Roy, et al., "Solid–Phase Synthesis of Dendritic Sialoside Inhibitors of Influenza A Virus Haemagglutinin," J.Chem. Soc., Chem. Commun., 1993, pp. 1869–1872.

Roy, et al., "Michael Addition of Poly–L–Lysine to N–Acryloylated Sialosides, Syntheses of Influenza A Virus Haemagglutinin Inhibitor and Group B Meningococcal Polysaccharide Vaccines," J. Chem. Soc., Chem. Commun. 1993, pp. 264–265.

Sigal, et al., "Polyacrylamides Bearing Pendant α–Sialoside Groups Strongly Inhibit Agglutination of Erythrocytes by Influenza Virus: The Strong Inhibition Reflects Enhanced Binding through Cooperative Polyvalent Interactions," J. Am. Chem. Soc., 118, 16, 1996, 3789–3800.

Choi et al., "Monomeric inhibitors of influenza neuraminidase enhance the hemagglutination inhibition . . . ", Chem. & Biol., 3:97–104, Feb., 1997.

Mammen et al., "Effective Inhibitors of Hemagglutination by Influenza Virus Synthesized from Polymers . . . ", J. Med. Chem, 34:4179–4190, 1995.

Tulip et al. Refined crystal structure of the influenza virus N9 neuraminidase–NC41 Fab complex. *J. Mol. Biol.* 227:122–148 (1992).

Tulip et al. Crystal Structures of two mutant neuraminidase–antibody complexes with amino acid substitutions in the interface, *J. Mol. Biol.* 227:149–59 (1992).

Varghese et al. The structure of the complex between influenza virus neuraminidase and sialic acid., the viral receptor. *Proteins: Structure, Function and Genetics* 14:327–332 (1992).

Von Itzstein et al., Rational design of potent sialidase–based inhibitors of influenza virus replication. *Nature* 363:418–423 (1993).

* cited by examiner

*Primary Examiner*—Donna C. Wortman
(74) *Attorney, Agent, or Firm*—Fish & Richardson PC

(57) ABSTRACT

The invention provides novel macromolecules, methods for their preparation, pharmaceutical formulations thereof and their use as anti-influenza agents. The invention also provides a novel diagnostic method which can be used for detection of all types of influenza A and B virus. The macromolecular compound of the invention has attached to it one or more molecules (neuraminidase binders) which bind to the active site of influenza virus neuraminidase but which are not cleaved by the neuraminidase.

41 Claims, No Drawings

MACROMOLECULAR NEURAMINIDASE-BINDING COMPOUNDS

This invention relates to a new class of chemical compounds and their use in medicine. In particular the invention provides novel macromolecules, methods for their preparation, pharmaceutical formulations thereof and their use as anti-influenza agents. The invention also provides a novel diagnostic method which can be used for detection of all types of influenza A and B virus.

BACKGROUND OF THE INVENTION

Influenza A and B viruses are major causes of acute respiratory disease, resulting in an estimated 30–50 million infections annually in the United States alone. Influenza A has been responsible for major epidemics, such as the "Spanish Flu" of 1919 which killed millions of people. Influenza remains a difficult disease to control, resulting in significant morbidity, and mortality largely due to secondary infection in eldery or debilitated patients. Vaccines are continually being rendered obsolete by antigenic shift or drift, and consequently immunization is only about 70% effective in preventing infection. The only drugs approved by regulatory authorities for treatment of influenza are amantidine and rimantidine, which are ineffective against influenza B, and are known to have serious side-effects.

Many viral and bacterial infections may present with symptoms similar to those of influenza. The rapid identification of respiratory viruses would enable physicians to use the most appropriate therapy early in the illness. For example, an early and accurate diagnosis would allow decisions regarding the use of antibacterial therapy and hospitalisation of children and the elderly.

Laboratory tests for the identification of viruses in clinical material are widely used, and a variety of different detection methodology is available. The textbook, "Laboratory Diagnosis of Viral Infections", Marcel Dekker 1992, Ed E. H. Lennette generally discusses methods which are used for a wide range of viruses, including influenza virus.

A number of tests are available for the diagnosis of influenza A and B. The traditional method of identifying influenza viruses has been the use of cell culture, which is highly sensitive and specific. Unfortunately, the time required for culture, isolation and identification of influenza virus can range between 2 and 10 days, thus making it virtually useless in guiding the physician to an appropriate therapy. Since influenza virus infection is normally self-limited, diagnosis must be rapid if therapy is to be effective.

In addition to the cell culture methods for detecting influenza, there have recently become available a few rapid direct tests, which are specific for influenza A. Thus, a monoclonal immunofluorescence assay (IFA) has been reported (Spada, B. et al, J. Virol. Method, 1991 33 305) and at least one rapid enzyme immunoassay (EIA) is available (Ryan-Poirier, K. A. et al, J. Clin. Microbiol., 1992 30 1072). A number of comparisons of these rapid detection methods for influenza A have been reported; see for example Leonardi, G. P. et al, J. Clin. Microbiol., 1994 32 70, who recommended that direct specimen testing be used together with culture isolation, so as to permit both identification of the virus in time to institute therapy and infection control measures, and to monitor the antigenic constitution of influenza strains prevalent in the community.

The IFA method is reported to be labor-intensive, and requires considerable technical expertise, with the results often being difficult to interpret. On the other hand, the EIA (Directigen FLU-A; Becton Dickinson Microbiology Systems) method gave a high level of false-positive results, and it has been recommended that this assay should be used in laboratories only as an addition or substitute for direct immunofluorescence tests (Waner, J. L. et al, J. Clin. Microbiol., 1991 29 479).

As well as the problems mentioned above with the currently available rapid assays for influenza, there are other fundamental deficiencies in some of these methods. Firstly, none of the available assays can detect influenza B, which means that even a negative test result would leave the physician uncertain about the type of therapy that should be used. Secondly, if a rapid immunoassay method depends on the use of antibodies to one of the influenza A proteins, there may be a serious problem in detecting new strains of the virus which have undergone a drift or shift in the structure of the antigenic proteins. Influenza A is notorious for its propensity to undergo such changes.

Another type of rapid assay for influenza viruses has been described in a series of patent specifications (see for example Liav, A. et al, PCT Patent Application No. 92/12256). The method involves the use of a chromogenic substrate for the influenza neuraminidase enzyme. In other words the assay depends on visualising a dye, which is formed when the influenza neuraminidase cleaves a special sialic acid-dye conjugate molecule. This technique appears to offer limited specificity, because it could not readily distinguish between the presence of viral neuraminidase and other forms of the enzyme, particularly bacterial neuraminidase. It may also have low sensitivity because of the relatively slow activity of viral neuraminidase.

Influenza A and B have two major surface glycoproteins, hemagglutinin (HA) and the enzyme neuraminidase (NA), which are both essential for infectivity. It is believed that HA is necessary for the virus to attach to cells whereas NA is needed for release of the virus from cell surfaces. There are typically about 600 trimeric HA and about 50 copies of the NA tetramer units on the surface of each virus particle. Both HA and NA therefore are attractive potential targets in the search for anti-influenza drugs, but to date no anti-influenza drugs that work at either of these sites are available for clinical use.

Influenza virus hemagglutinin binds to the sialic acid containing glycoproteins and glycolipids on cell-surface receptors, thereby initiating the process of attachment of the virus to a cell and subsequent infection. The strength of the binding of a virus particle to the cell membrane appears to depend on the interaction of multiple copies of the influenza HA with multiple sialic acid groups on the cell surface.

Using this concept of a polyvalent interaction, several workers have reported the synthesis of macromolecules containing two or more sialic acid derivatives which act as hemagglutinin inhibitors. Although some strong HA inhibitors have been discovered, none of these polyvalent macromolecules has been shown to prevent influenza infection in vivo. Recent papers by Whitesides and co-workers (J. Amer. Chem. Soc., 1996 118 3789–3800; J. Medicinal Chem., 1995 38 4179–4190) have summarised the various efforts which have used this approach to the design of inhibitors of influenza hemagglutinin.

There are several known inhibitors of NA, most of which are close analogues of neuraminic acid, the enzyme's natural substrate, such as 2-deoxy-2,3-didehydro-N-acetylneuraminic acid (DANA) (Meindl et al, Virology, 1974 58 457–63). International Patent Application No. WO 91/16320 describes analogs of DANA which are very active, both in vitro and in vivo, against influenza A and B neuraminidase. One of these compounds (Compound I, designated GG167 or 4-guanidino-Neu5Ac2en) is in clinical trial, and shows promise for the treatment of influenza (Hayden, F. G. et al, J. Amer. Med. Assoc., 1996 275 295).

Compound (I)

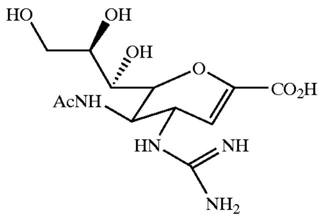

GG167

More recently, aromatic compounds with neuraminidase-inhibitory activity have been described in U.S. Pat. No. 5,453,533 by Luo et al and U.S. Pat. No. 5,512,596 by Gilead Sciences, Inc., and analogues of compound (I), in particular compounds in which the side-chain at carbon 6 is ether-linked, have been described in International Patent Application No. WO 96/26933 by Gilead Sciences, Inc. and in C. Kim et al, J. Amer. Chem. Soc., 1997 119 681.

Several research groups have attempted to find simpler or more potent analogues of compound (I), but reports to date (e.g. Bamford M. J., J. Chem. Soc. Perkin Trans. I, 1995, 1181) indicate that any changes to the structure of compound (I), particularly at the glycerol side chain, are likely to reduce the neuraminidase-binding properties. In addition, in contrast to the situation with HA, there do not appear to be any known macromolecular or polymeric inhibitors of neuraminidase. Sialic acid-containing polymers have been described in U.S. Pat. No. 5,192,661 by Roy et al and in U.S. Pat. No. 5,571,836 by Bovin et al, but these compounds were synthetic polysialosides designed for use as antigens or as binders of haemagglutinin.

SUMMARY OF THE INVENTION

In a first aspect, the invention provides macromolecular compounds which have attached to them one or more molecules which bind to the active site of influenza virus neuraminidase; these molecules are referred to herein as "neuraminidase binders". Preferably the neuraminidase binder is attached to the molecule via a spacer or linker group so that the neuraminidase binder is not sterically hindered by the backbone of the macromolecule. The neuraminidase binder may be any agent which binds to the active site of influenza virus neuraminidase, provided that it is not cleaved by the enzyme. The binding need not be irreversible, but the binding group should have a high binding affinity, preferably an $IC_{50}$ of $10^{-6}$ M or less.

The invention particularly relates to a new class of chemical compounds and their use as therapeutic and diagnostic agents for the treatment and detection of influenza A and B. More specifically the invention concerns macromolecules which have attached to them neuraminic acid (sialic acid) derivatives which bind to neuraminidase of influenza A or B, and which optionally also have a functionality which allows the compounds to be bound to a surface, or which can be used as a detectable label.

Surprisingly, we have found that when compound (I) is functionalised through the 7-position of the sialic acid structure, it can be attached to large synthetic or natural polymers to give complexes which inhibit influenza A and B neuraminidase, and which can prevent or inhibit influenza infection. Rather than destroying the influenza neuraminidase-binding properties of compound (I), we find that when multiple numbers of this and similar compounds are linked through their 7-position by a suitable spacer to a variety of macromolecules the average binding per sialic acid group is not substantially reduced. Thus through the binding to neuraminidase the macromolecules are tightly bound to the virus, and possibly because of the size and steric effects of the complexes, the infectivity of the influenza virions is reduced. Such macromolecular compounds can also be used to enable the detection of influenza A and B virus through their ability both to bind the influenza virus selectively and at the same time to be bound to a surface or to a detectable linking group.

The biological activity of the macromolecular compounds of the invention and the diagnostic method of the invention are both based on the use of ligands on the macromolecules that are able to bind specifically to the active site of influenza virus neuraminidase, or functionalised derivatives of such compounds, as binding and/or detecting agents to identify influenza virus in clinical specimens. The term "neuraminidase binders" is used hereinafter to refer to these compounds and their functionalized derivatives. The method and compounds of the invention can function either in the presence or the absence of compounds binding non-specifically to influenza virus neuraminidase.

In a preferred embodiment, the present invention provides a compound of formula (II):

$$(X—Y)_n—M—(Z)_m \qquad (II)$$

wherein X is a neuraminidase-binding 2,3-dehydro-sialic acid derivative (2) which is linked at the 7-position via a spacer group Y to a macromolecule M, and Z is an optional extra substituent on the macromolecule.

The neuraminidase-binding moiety X is a sialic acid derivative of formula (2)

(2)

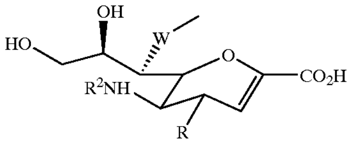

in which the spacer Y connects to the W group, and wherein R represents an azido group, an unsubstituted or substituted guanidino group, or an unsubstituted or substituted amino group;

$R^2$ represents $COCH_3$, $COCF_3$, $SO_2CH_3$ or $SO_2CF_3$;

W represents O(C═O)NH, O(C═S)NH, NH(C═O)NH or NH(C═S)NH and is attached through the NH to group Y;

m is an integer between 0 and 1000; and n is an integer between 1 and 1,000.

The spacer group Y is an optionally substituted chain of up to 1000 atoms chosen from carbon, nitrogen, oxygen and sulphur.

The macromolecule M is a synthetic or natural polymer, protein, antibody or enzyme of molecular weight from $10^4$ up to $10^7$.

The Y group is generally linked covalently to the macromolecule M, but may also be bound through non-covalent attachment, for example when M is avidin and Y has a terminal biotin group.

The second and optional substituent Z can be a group that binds hemagglutinin, such as a 2-linked sialic acid derivative, or a group that can act as a detectable label, such as a biotin or fluorescent molecule, or it can be an antibody-binding hapten. The optional substituent z can also be an enzyme such as horseradish peroxidase (HRP) or alkaline phosphatase (AP) which can be used to enable detection of influenza. Alternatively, the group Z can be a group with a terminal functionality that is suitable for binding the macromolecule to a surface, such as $NH_2$, SH, $CO_2H$, CHO, or $CH═CH_2$.

In another preferred embodiment, the invention provides neuraminidase binders of formula (IIA):

$$(X'—Y)_n—M—(Z)_m \qquad (IIA)$$

wherein X' is a neuraminidase-binding cyclohexenyl derivative of formula (2a), (2a)

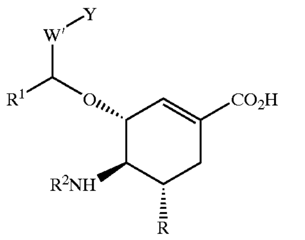

which is linked through the ether side-arm,

R, $R^2$,Y, n and m are as defined above for formula (2), and $R^1$ and W' are lipophilic $C_1$–$C_{12}$ alkyl or alkylene groups which are optionally substituted by one or more halogen atoms or alkoxy, haloalkoxy or optionally substituted aryl groups.

Suitable spacer groups Y include, but are not limited to, aminoalkyl groups, (poly)amino acids, linear peptides, oligosaccharides and polysaccharides, polyethylene glycol units, and amino-dialkylureas, any of which may be used alone or in combination. Typically the spacer group Y has a terminal amino group, which is used to form an amide or Schiffs base linkage on to the macromolecule M.

Suitable substituents of the guanidino or amino groups R include methyl, ethyl, allyl, amino, cyano or nitro.

Suitable macromolecules M include proteins, enzymes, antibodies, water-soluble synthetic polymers such as polyacrylic acids and polyacrylamides, polysaccharides and polyaminoacids. Macromolecules which are particularly suitable for use in diagnostic applications include bovine serum albumin (BSA), horseradish peroxidase (HRP), avidin and related proteins such as streptavidin or neutravidin, and immunoglobulins.

Macromolecules which are particularly suitable for use in compounds of the invention to be used in the treatment of influenza include polysaccharides, synthetic polymers such as polyacrylamides, polyethylene glycols, polyureas, polyacids, polyesters, polyamides and various co-polymers such as N-(2-hydroxy-propyl)methacrylamide (HMPA), which are known to be safe for administration to humans. The person skilled in the art will be aware of other pharmaceutically-acceptable polymers.

One preferred group of compounds of the invention comprises compounds (II), in which X is a GG167 derivative of formula (2) wherein:

R is guanidine, $R^2$ is acetyl, W is the group O(═CO)NH and the spacer Y is a chain made up of between 6 and 60 carbon, nitrogen and oxygen atoms.

The macromolecules of formula (II) are inhibitors of influenza A and B neuraminidase and possess anti-influenza activity. Thus in a second aspect of the invention there is provided a pharmaceutical composition for treatment of influenza A or influenza B comprising a compound of the invention, preferably a compound of formula (II) or formula (IIA), or a pharmaceutically-acceptable derivative thereof, together with a pharmaceutically-acceptable carrier.

In a third aspect there is provided a method of treatment of influenza infection in a mammal, including man, comprising the step of administering an effective amount of a compound of the invention, preferably a compound of formula (II) or formulae (IIA) or a pharmaceutically acceptable derivative thereof, to a mammal in need of such treatment.

There is also provided in a fourth aspect the use of a compound of the invention, preferably a compound of formula (II) or formula (IIA) for the manufacture of a medicament for the treatment of an influenza viral infection.

The compounds of the invention may also be used in combination with other therapeutic agents, for example other anti-infective agents, particularly other anti-viral agents. The invention thus provides in a further aspect a pharmaceutical composition comprising a compound of the invention, preferably a compound of formula (II) or formula (IIA) or a pharmaceutically acceptable salt or derivative thereof together with one or more further therapeutically active agent, in particular an anti-viral agent, together with a pharmaceutically-acceptable carrier.

The invention also provides in another aspect a method of detection of influenza virus, comprising the step of exposing a sample suspected to include said virus to a compound of the invention which is able to bind specifically to the active site of influenza virus neuraminidase.

The method of the invention is applicable to all types of influenza A and influenza B.

For the detection of influenza the compounds of the invention (II) may be attached to a surface, either by covalent bonding or by non-specific binding. The spacer group Y should be sufficiently long that the neuraminidase binding units X are exposed on the surface of the imacromolecule M and accessible to a virus particle.

For the detection of influenza the method of the invention may use selective capture with a compound of formula (II) and thereby concentration of the virus, followed by detection of the virus using any convenient conventional method; the detection method need not have inherent selectivity. For example, the binder (II) may be attached to a support material, such as a membrane or polymer, such that virus particles will be selectively captured and concentrated when a sample is passed over or through the support. Therefore in one preferred embodiment of the invention, the group Z terminates in a functionality able to bind to a surface. Many suitable functionalities are known in the art.

Alternatively, a selective detection approach may be used; the virus particles in a sample may for example be non-specifically captured and then exposed to a macromolecular neuraminidase binder (II) which includes a detectable label Z, under conditions such that the binder attaches selectively to the influenza neuraminidase on the surface of the viral particle. The detectable label is then detected using any convenient method. For some detection systems, it is convenient to focus the sample into a confined area, for example a spot or a line on a surface. This may be achieved by a variety of methods; for example, the sample may be suspended or non-selectively captured on to a filter or other support material, and then exposed to the labelled binder as above.

In another alternative aspect the invention may use a combination of selective capture and selective detection to provide a simple and sensitive two-stage method of detecting influenza virus. This makes use of the fact that influenza virus particles typically have about one hundred neuraminidase molecules spread over their spherical surface (White, D. O., Curr. Top. Microbiol. Immunol., 1974 63 1–48), and can therefore attach to more than one binder at the same time.

Thus, a neuraminidase binder compound (II) may be attached to a support, for example as a narrow band across a length of porous membrane. The test sample is then applied at the other end of the membrane and allowed to flow across the band of bound compound. Any influenza virus particles in the test sample will be trapped by the membrane-bound compound (II) and thus retained in the narrow band. In the second stage of the test, a detectable label attached to another neuraminidase binder (II) is allowed to flow through the membrane across the band of bound influenza virus particles. The presence of influenza virus is then shown by an observable change in the membrane at the site of the bound compound. It is contemplated that the method and compounds of the invention are suitable for use with the Biostar Optical Immunoassay (OAI) platform, which is described inter alia in U.S. Pat. No. 5,418,135 by Miller et al.

A very large number of suitable detection systems is known in the art, for example biotin-streptavidin, enzymic systems such as horseradish peroxidase or alkaline phosphatase, fluorescence systems, chemiluminescence systems, colloidal gold, radioactive labels and agglutination systems. It is contemplated that colloidal gold coated with a compound of the invention (II) will be a particularly convenient detectable label. Similarly, compounds of the invention wherein the macromolecule M is horseradish peroxidase are expected to be ideal for the ready detection of influenza. The skilled person will readily be able to select a suitable detection system and to optimise conditions for detection, using normal trial and error experimentation.

The compounds of the invention of formula (II) and their pharmaceutically acceptable salts and derivatives may be prepared by various methods which include those described below. The methods of preparation outlined below form another aspect of the invention.

DETAILED DESCRIPTION OF THE INVENTION

The invention will now be described in detail by way of reference only to the following non-limiting examples.

Examples of compounds of the invention include those of Formula (3) in which M is a protein, as listed in Table 1 below.

TABLE 1

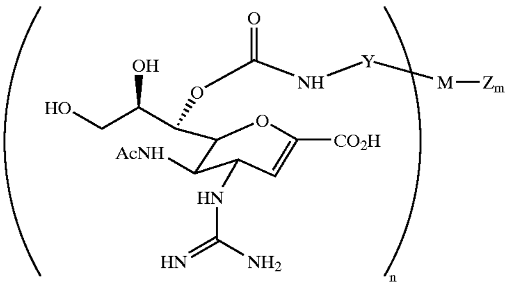

(3)

| Compound No. | Spacer Y | Protein M | n | Substituent Z | No of m |
|---|---|---|---|---|---|
| 3a | $(CH_2)_6NHCO(CH_2)_5NHCO(CH_2)_6CO$— | BSA | 30 | Biotinamidocaproyl | 8 |
| 3b | $(CH_2)_6NHCO(CH_2)_5NHCO(CH_2)_6CO$— | Bovine IgG | 60 | Biotinamidocaproyl | 18 |
| 3c | $(CH_2)_6NH[CO(CH_2)_5NH]_3CO(CH_2)_5NHCO(CH_2)_6CO$ | BSA | 6 | — | — |
| 3d | $(CH_2)_6NH[CO(CH_2)_5NH]_3CO(CH_2)_5NHCO(CH_2)_6CO$ | BSA | 12 | — | — |
| 3e | $(CH_2)_6NH[CO(CH_2)_5NH]_3CO(CH_2)_5NHCO(CH_2)_6CO$ | HRP | 3 | — | — |
| 3f | $(CH_2)_6NH[CO(CH_2)_5NH]_3CO(CH_2)_5NH$— | HRP | 2 | — | — |
| 3g | $(CH_2)_6NH[CO(CH_2)_5NH]_4CO(CH_2)_6CO$ | Bovine IgG | 42 | — | — |
| 3h | $(CH_2)_6NH[CO(CH_2)_5NH]_4CO(CH_2)_6CO$ | Bovine IgG | 12 | — | — |
| 3i | $(CH_2)_6NH[CO(CH_2)_5NH]_4CO(CH_2)_6CO$ | Bovine IgG | 24 | — | — |
| 3j | $(CH_2)_6NHCO_2[CH_2CH_2O]_{70}CH_2CH_2NHCO(CH_2)_6CO$ | Bovine IgG | 20 | — | — |

Further examples of compounds of the invention include those of Formula (4) in which M is the protein avidin, which non-covalently binds the group X—Y, and also has covalently attached ligands Z as listed in Table 2 below.

TABLE 2

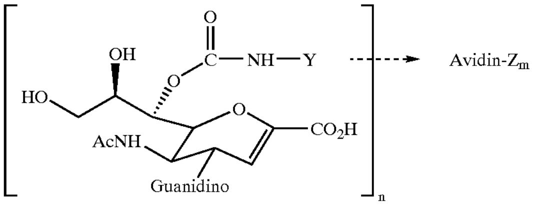

(4)

| Compound No. | Spacer Y | n | Substituent Z | m |
|---|---|---|---|---|
| 4a | $(CH_2)_6NH(COCH_2NH)_2COCH_2NH$-Biotin- | 4 | — | — |
| 4b | $(CH_2)_6NH(COCH_2NH)_2COCH_2NH$-Biotin- | 4 | Biotinamidocaproyl | 5 |

TABLE 2-continued

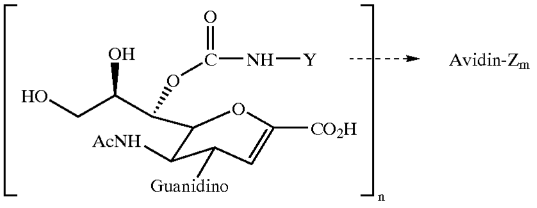

(4)

| Compound No. | Spacer Y | n | Substituent Z | m |
|---|---|---|---|---|
| 4c | $(CH_2)_6NH(COCH_2NH)_2COCH_2NH$-Biotin- | 4 | Biotinamidocaproyl | 10 |
| 4d | $(CH_2)_6NH(CO(CH_2)_5NH)_3CO(CH_2)_5NH$-Biotin | 4 | Biotinamidocaproyl | 10 |
| 4e | $(CH_2)_6NHCO(CH_2)_5NHCOCH_2(OCH_2CH_2)_{16}NH$-Biotin | 4 | Biotinamidocaproyl | 8 |

Further examples of compounds of the invention in which M is a synthetic polymer include those of Formula (5) as shown below in Table 3, wherein the substituents on the sialic acid group (2) are $R^2$=Ac, R=guanidine and W is OCONH.

TABLE 3

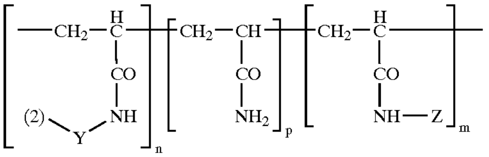

(5)

| Compound No. | Spacer Y | n | p | Substituent. Z | m |
|---|---|---|---|---|---|
| 5a | $(CH_2)_6$ | 1 | 13 | — | — |
| 5b | $(CH_2)_6$ | 1 | 7 | — | — |
| 5c | $(CH_2)_6NHCONH(CH_2)_6$ | 1 | 9 | — | — |
| 5d | $(CH_2)_6NH(CO(CH_2)_5NH)_3CO(CH_2)_5$ | 1 | 8 | — | — |
| 5e | $CH_2CH_2OCH_2CH_2OCH_2CH_2$ | 1 | 8 | — | — |
| 5f | $(CH_2)_6$ | 1 | 500 | — | — |
| 5g | $(CH_2)_6NH[CO(CH_2)_5NH]_3CO(CH_2)_5$ | 1 | 20 | — | — |
| 5h | $(CH_2)_6NH[CO(CH_2)_5NH]_3CO(CH_2)_5$ | 1 | 50 | — | — |
| 5i | $(CH_2)_6NH[CO(CH_2)_5NH]_3CO(CH_2)_5$ | 1 | 45 | benzyl | 5 |
| 5j | $(CH_2)_6$ | 1 | 50 | — | — |
| 5k | $(CH_2)_6$ | 1 | 45 | benzyl | 5 |
| 5l | $(CH_2)_6$ | 2 | 40 | hexyl-biotin | 1 |
| 5m | $(CH_2)_6$ | 2 | 40 | hexyl-fluorescein | 1 |
| 5n | $(CH_2)_6$ | 1 | 20 | $CH_2CH_2SH$ | 1 |

Further examples of compounds of the invention in which M is a dextran backbone (Molecular weight 500,000) include those represented by formula (6) as shown below in Table 4, wherein the substituents on the neuraminidase binding group (2) are $R^2$=Ac, R=guanidine and W is OCONH. The integers n, m and p in the formula (6) give the percentage of the glucose units in the dextran backbone which are substituted by the particular groups, ie when n, m and p do not add up to 100 the remaining dextran backbone is made up of unsubstituted glucose units. It should also be remembered that there are three possible points of attachment for the various ligands bound to each unit of the dextran backbone.

TABLE 4

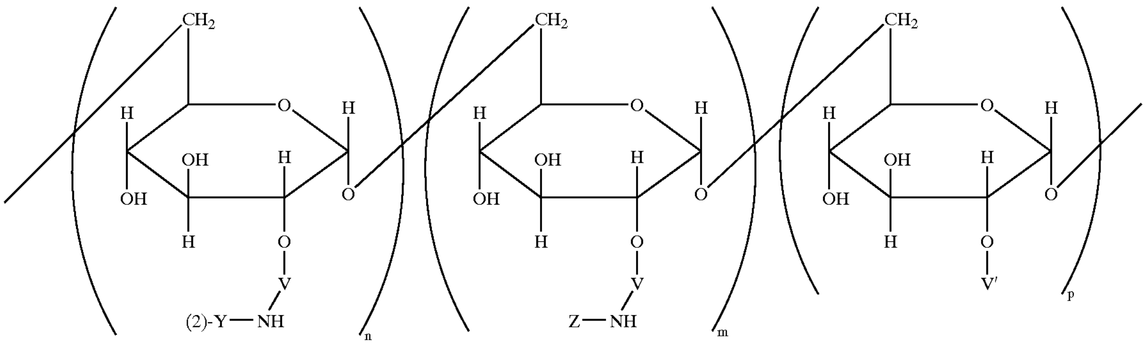

(6)

| Compound No. | Spacer Y | n % | Link V | Substituent Z | m % | V' | p % |
|---|---|---|---|---|---|---|---|
| 6a | $(CH_2)_6$ | 4 | C═O | benzyl | 17 | H | — |
| 6b | $(CH_2)_6$ | 3 | $CH_2CO$ | benzyl | 17 | $CH_2CO_2H$ | 20 |
| 6c | $(CH_2CH_2O)_2CH_2CH_2$ | 4 | $CH_2CO$ | benzyl | 16 | $CH_2CO_2H$ | 20 |
| 6d | $(CH_2)_6NHCO_2[CH_2CH_2O]_{70}CH_2CH_2$ | 7 | $CH_2CO$ | benzyl | 16 | $CH_2CO_2H$ | 17 |
| 6e | | 4 | C═O | benzyl | 16 | H | — |
| 6f | $(CH_2)_6$ | 3 | $CH_2CO$ | benzyl | 10 | $CH_2CO_2H$ | 27 |
| 6g | $(CH_2)_6NH[CO(CH_2)_5NH]_4$— | 2 | C═O | — | — | H | — |
| 6h | $(CH_2)_6NH[CO(CH_2)_5NH]_4$— | 1 | C═O | $NH(CH_2)_6S$-2-sialic acid | 5 | H | — |
| 6i | — | 0 | C═O | benzyl | 16 | H | — |
| 6j | — | 0 | $CH_2CO$ | benzyl | 16 | $CH_2CO_2H$ | 24 |

Further examples of compounds of the invention include those in which the macromolecule M is a dextran or polyacrylic acid backbone, and wherein the substituents on the sialic acid group (2) are R2=Ac, R=guanidine and W=OCONH, and wherein the extra substituent Z is for example a benzyl group, a biotin molecule or a fluorescein-containing group.

It will be appreciated by those skilled in the art that reference herein to treatment extends to prophylaxis as well as to the treatment of established infections or symptoms. Treatment is preferably commenced before or at the time of infection and continued until virus is no longer present in the respiratory tract. In general a suitable dose of a compound of the invention will be in the range of 0.1 to 100 mg/Kg/day, preferably in the range of 0.2 to 20 mg/Kg/day.

Suitably treatment is given 1–4 times daily and continued for 3–7 days post infection. The desired dose may be given in a single dose, or as divided doses at appropriate intervals.

While it is possible that, for use as a therapy, a compound of the invention may be given as the raw chemical, it is generally preferable to present the active ingredient as a pharmaceutical formulation. The invention thus provides a pharmaceutical formulation comprising compounds of formula (II) or an acceptable salt or derivative thereof, together with one or more pharmaceutically acceptable carriers therefor and, optionally, other therapeutic and/or prophylactic agents. Pharmaceutical formulations include those for oral, nasal or topical administration or in a form suitable for inhalation or insufflation into the respiratory tract. The formulations may, where appropriate, be conveniently presented in discrete dosage units and may be prepared by any of the methods well known in the art of pharmacy.

In general the compounds of the invention may be administered in the form of a solution or a suspension or as a dry powder. For administration to the respiratory tract according to the method of invention the neuraminidase inhibitors may be administered by any of the methods and formulations employed in the art for administration to the respiratory tract.

Solutions and suspensions will generally be aqueous and for example prepared from water alone or water and a physiologically acceptable co-solvent (for example ethanol, propylene glycol, polyethylene glycols such as peg 400). Such solutions or suspensions may additionally contain other excipients for example preservatives (such as benzalkonium chloride), solubilising agents/surfactants such as polysorbates (e.g. Tween 80), buffering agents, isotonically-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied to the nasal cavity by conventional means, for example with a dropper, pipette or spray. The formulations may be provided in single or multiple dose form. A spray may be achieved for example by means of a metering atomising spray pump. Administration to the respiratory tract may also be achieved by means of an aerosol formulation in which the compound is provided in a pressurised pack with a suitable propellant such as a chlorofluorcarbon (CFC) or other suitable gas.

Alternatively the compounds may be provided in the form of a dry powder, for example a powder mix of the compound in a suitable base such as lactose, starch, starch derivatives and polyvinylpyrrolidine. Consequently the powder will form a gel in the nasal cavity. In formulations intended for administration to the respiratory tract, including intranasal formulations, the compound will generally have a small particle size, for example of the order of 5 microns or less. Such a particle size may be obtained by means known in the art.

The compounds of the invention are prepared in several stages, the first part generally being the synthesis of a neuraminidase-binding sialic acid derivative of formula X—Y, wherein X and Y are as defined above.

Methods for the synthesis of sialic acid derivatives (2) with suitable functionality at the 7-position are described in British Patent Application No. 9516276.4, and in International Patent Application No. PCT/AU97/00190.

Examples of suitable sialic acid derivatives X—Y are shown below in Table 5, wherein the groups R2, R and W are the substituents on moiety X as described above.

TABLE 5

| Compound No. | $R^2$ | R | W | Spacer Y |
| --- | --- | --- | --- | --- |
| 2a | Ac | Guanidine | OCONH | $(CH_2)_6NH_2$ |
| 2b | Ac | Guanidine | OCONH | $(CH_2)_6NHCO(CH_2)_5NH_2$ |
| 2c | Ac | Guanidine | OCONH | $(CH_2)_6NH(CO(CH_2)_5NH)_3CO(CH_2)_5NH_2$ |
| 2d | Ac | Guanidine | OCONH | $(CH_2CH_2O)_2CH_2CH_2NH_2$ |
| 2e | Ac | Guanidine | OCONH | $(CH_2)_6NH(CO(CH_2)_5NH)_3CO(CH_2)_5NH$-Biotin |
| 2f | Ac | Guanidine | OCONH | $(CH_2)_6NHCONH(CH_2)_6NH_2$ |
| 2g | Ac | Guanidine | OCONH | $(CH_2)_6NHCO_2[CH_2CH_2O]_{70}CH_2CH_2NH_2$ |

The second part of the preparation of the compounds of the invention involves attachment of the neuraminidase-binding units X—Y to the macromolecule M. For covalent attachment of units X—Y to macromolecules M of a protein type, the conjugation can generally be carried out using standard cross-coupling methods which are well known (e.g. S. S. Wong, "Chemistry of Protein Conjugation and Cross-Linking" CRC Press, 1991; G. T. Hermanson, "Bioconjugate Techniques" Academic Press, 1996).

In the case of synthetic polymers, the units X—Y may be added to a preformed polymer backbone which has suitable activated substituents. For example, if group Y has a terminal amino functionality it may be reacted with activated ester substituents on a polyacrylate backbone. Alternatively, units X—Y with a suitable polymerisable substituent, such as a terminal olefin may be polymerised or preferably co-polymerised with another olefin, to generate the macromolecular backbone. See for example R. Roy, Trends in Glycoscience and Glycotechnology, 1996 8 79–99; N. V. Bovin and H. J. Gabius, Chem. Soc. Reviews., 1995 413)

EXAMPLE 1

Preparation of a GG167-Bovine Serum Albumin-Biotin conjugate (3a)

(a) Preparation of 5-acetamido-7-(6'-(6"-aminocaproyl) aminohexyl)-carbamoyloxy-4-guanidino-2,3,4,5-tetradeoxy-D-glycero-D-galacto-non-2-enopyranosonic Acid (2b) (7-(6-Aminocaproyl)amino-hexylcarbamoyloxy-GG167)

6-(t-Butyloxycarbonylamino)caproic acid (34 mg, 147 μmol) was dissolved in a mixture of acetone (2.5 ml), water (100 μl), N-methyl morpholine (4 μl, 36 μmol) and triethyl amine (21 μl, 147 μmol)). The solution was cooled to −12° C., and then isobutyl chloroformate (21 μl, 161 μmol) was added. The solution was stirred for 12 minutes.

Methyl 5-acetamido-7-(6'-aminohexyl)-carbamoyloxy-4-guanidino-8,9-monocarbonyldioxy-2,3,4,5-tetradeoxy-D-glycero-D-galacto-non-2-enopyranosonate trifluoroacetic acid salt (79 mg, 92 μmol) was dissolved in water/acetone (1:1, 2 ml) containing triethylamine (40 μl, 287 μmol). This basic solution was cooled to 0° C. and added as a single portion to the previous reaction mixture. The mixture was allowed to warm to room temperature and stirred for 4 hours.

The solvents were removed under reduced pressure. The crude product was taken up in methanol/water (1:1, 4 ml) and then triethylamine (1 ml) was added. This solution was stirred overnight under argon. The solvents were removed on a rotary evaporator and the residue was dissolved in methanol and adsorbed on to silica gel (1.5 g). Chromatography on silica gel (10 g), eluting with ethyl acetate/isopropanol/water (100/75/25) gave the product (53 mg, 77 μmol, 84%).

$^1H$ n.m.r. ($CD_3OD$, 200 M Hz) δ5.67 (d, J 2.6 Hz, 1H); 5.03 (m, 1H); 4.62 (m, 1H); 4.49 (m, 1H); 4.23 (m, 1H); 4.12 (m, 1H); 3.77 (m, 1H); 3.62 (m, 1H); 3.12 (m, 6H); 2.22 (t, J 8 Hz, 2H); 2.0 (s, 3H); 1.5 (m, 23H).

The t-Boc protected sugar was dissolved in ethyl acetate/toluene and evaporated to dryness. The material was dissolved in trifluoroacetic acid (3 ml) and stirred at room temperature under argon for 1 hour. The solvent was removed under reduced pressure, and residual trifluoroacetic acid was removed by co-evaporation first with dichloromethane, then 3 portions of water/methanol. The sample was then dissolved in water, filtered and lyophilised to give the product (141 mg, 152 μmol) as the tris TFA salt. Mass spectrum (FAB): 588 (M+1)

$^1H$ n.m.r. ($CD_3OD$, 300 M Hz) δ5.92 (d, J 2.6 Hz, 1H) ; 5.01 (m, 1H); 4.60 (dd, J 10, 3 Hz, 1H); 4.44 (dd, 9, 3 Hz, 1H); 4.23 (m, 1H); 4.05 (m, 1H); 3.67 (dd, 13, 4 Hz, 1H); 3.52 (dd, 13, 7 Hz, 1H); 3.16 (m, 5H); 2.96 (;t, 8 Hz, 2H); 2.25 (t, 8 Hz 2H); 2.00 (s, 3H); 1.7–1.3 (m, 14H).

(b) Preparation of the Conjugate between the GG167 Derivative (2b) and Bovine Serum Albumin-(6-aminocaproyl biotin)$_8$ Protein coupling buffer: 0.1N $NaHCO_3$/0.2M NaCl Dialysis buffer: 20 mM $KH_2PO_4$/0.15 M NaCl, pH 6.5

BSA-(caproyl-biotin)$_8$ (3 mg, 43 nmol, Pierce) was dissolved in the coupling buffer (7.5 ml) and stirred gently for 30 minutes.

Bis-(N-hydroxy sulfosuccinimide)suberate (12 mg, 21 μmol, Pierce) was dissolved in coupling buffer (1 ml) and added directly to a basic solution of compound (2b) from Example 1(a) (19.5 mg, 21 μmol) in coupling buffer (1.5 ml). The reaction was allowed to stir for 7.5 minutes. The BSA-biotin solution was then added dropwise to the derivatised-GG167 solution and the mixture was left to stir at room temperature for 1.5 hours. The solution was lyophilised, dissolved in water (3.0 ml) and dialysed against dialysis buffer (3×1.5 L, cellulose tubing, 12,000 MW cut off).

The mixture was lyophilised, taken up in water (2.5 ml) and desalted on a PD-10 column (Pharmacia), then lyophilised to give the product (3a) (2.5 mg).

The estimation of the sugar incorporation (30 GG167 units per protein molecule) was based upon a colorimetric assay for the guanidine group (Sakaguchi Reaction, see Can. J. Chem., 1958 36 1541).

EXAMPLE 2

Preparation of Bovine Serum γ Globulin-(6-aminocaproyl biotin)$_{18}$-(GG167-7-carbamate-1,6-diaminohexane-6-aminocaproic Acid Amide-suberic Acid Amide)$_{60}$ (3b)

Bovine γ globulin (3 mg, 20 nmol, Sigma) was dissolved in coupling buffer (1 ml) and stirred for 30 minutes.

N-Hydroxy sulfosuccinimidyl-N-Biotinyl-6-aminocaproate (1.8 mM, 280 μl, 0.5 μmol) in coupling buffer was added to the protein solution, and the reaction was stirred at room temperature for 1 hour.

The reaction mixture was then diluted to 7.5 ml with coupling buffer and reacted with bis(N-hydroxy sulfosuccinimidyl)suberate and GG167-7-carbamate-1,6-diaminohexane-6-aminocaproic acid amide from Example 1(a) above) under conditions identical to Example 1(b).

The yield of lyophilised γ-globulin conjugate (3b) was 2.5 mg.

EXAMPLE 3

Preparation of the Conjugate 3f between Compound 2c and Horseradish Peroxidase (HRP)

Compound 2c was coupled to HRP following the well established periodate oxidation methodology (see for example G. T. Hermanson, "Bioconjugate Techniques" Academic Press, 1996 472) to give compound 3f.

HRP (type IV-A, Sigma Aldrich P-6782, 5 mg, 114 nmol) was dissolved in sodium acetate/sodium chloride buffer (5 mM/150 mM, pH 4.5, 500 μl). To this was added freshly prepared sodium periodate solution (88 mM in sodium acetate/sodium chloride buffer, 50 μl, 4.4 mmol) and the reaction was allowed to stand in the dark at room temperature for 20 min. The mixture was chromatographed on a PD-10 column (Pharmacia Biotech, Sephadex G-25) pre-equilibrated with sodium acetate buffer (5 mM, pH 4.5), and the eluent was freeze dried.

The oxidized HRP was dissolved in sodium carbonate buffer (0.2M, pH 9.5, 1 ml) containing compound 2c (3.9 mg, 3.75 μmol) at 4° C., and the reaction was left to stand overnight at 4° C. A solution of sodium cyanoborohydride (5M in 1N NaOH, 10 μl, 50 μmol) was added and the reaction allowed to stand overnight at 4° C. A solution of ethanolamine (1M, pH 9.5, 50 μl, 50 μmol) was added and the reaction allowed to stand at room temperature for 30 min before chromatography on a PD-10 column, pre-equilibrated with distilled water. The eluent was freeze dried to give the HRP-compound 2c conjugate as a pale brown powder.

EXAMPLE 4

Preparation of Protein-GG167 Conjugates 3c, 3d and 3g–3j

Compounds 3c, 3d and 3g–3j were prepared by coupling the appropriate protein with either compound 2c or 2g using bis(N-hydroxy sulfosuccinimide)suberate and following a similar procedure to that described in Example 1, Part (b).

EXAMPLE 5

Preparation of a Biotinylated Complex (4d) between Avidin and a GG167-Biotin Conjugate (a) Preparation of 5-acetamido-7-(6'-(6"-(6'"-biotinylaminocaproyl)-triaminocaproyl)aminohexyl)-carbamoyloxy-4-guanidino-2,3,4,5-tetradeoxy-D-glycero-D-galacto-non-2-enopyranosonic acid (2e) was carried out using Boc-protected tetra(6-aminocaproic acid) and following a similar method to that described in Example 1.

(b) Avidin (3 mg, 0.0445 μmol) was dissolved in a solution of compound (2e) (0.5 mg, 0.434 μmol) in water (500 μl) at room temperature for 2 hours. To this resulting solution were added sulfo-N-hydroxysuccinimido-caproylamino-Biotin (Pierce #21335) (1000 μg, 1.798 μmol) and a solution of sodium bicarbonate (1000 μg, 11.9 μmol) in water (240 μl). The whole mixture was allowed to stand at room temperature for 45 minutes, then placed in a dialysis tube (molecular weight cut off 12,000). The tube was dialysed successively against 50 mM $NaHCO_3$ solution (4×250 ml) and water (8×250 ml), with the immersion time being 45 minutes in each case. The tube was finally dialysed against water (500 ml) at room temperature overnight. The resulting solution from the dialysis tube was adjusted to pH 6.5–7.0 with sodium bicarbonate and then freeze-dried to afford the title complex (4c) (3 mg, 89%) as a white solid. The complex comprised four GG167-Biotin molecules bound via the four avidin binding sites and then the avidin backbone substituted with about eight to ten covalently-bound biotin ligands. A diagram of the complex is shown in FIG. 1, wherein A represents avidin, B represents biotin and S represents the GG167 sugar molecule.

EXAMPLE 6

Preparation of Polyacrylamides (5a)–(5e) Substituted with Various GG167-ligands (a) Poly(N-(acryloyloxy)succinimide) (pNAS) was prepared from N-(acryloyloxy)succinimide as described by Ferruti et al. (Polymer, 1972, 13, page 462). The $^1H$ n.m.r. spectrum and infrared spectrum of the pNAS were consistent with those previously reported in the literature. A sample of the batch of pNAS was converted into polyacrylamide by treatment with conc. ammonia for several hours at room temperature and the molecular weight of the dialysed polyacrylamide was found to be approximately 50,000 using viscometry.

(b) Polyacrylamides (5a)–(5e) incorporating various GG167 derivatives were prepared from the one batch of pNAS following the general method outlined below for compound (5c).

A solution of pNAS (10 mg, 59 μmol of NAS) in dimethylformamide (DMF, 0.5 ml) was added, to a solution of compound (2f) (3.8 mg, 6.2 μmol) in DMF (0.5 ml) at room temperature with stirring. Triethylamine (10 μl, 70 μmol) was added and the clear solution was stirred overnight at room temperature, then heated at 65° for five hours and stirred overnight again at room temperature. Dilute aqueous ammonia (6 ml of 3% solution) was added to the reaction mixture and the clear solution was allowed to stand for 24 hours at room temperature. The reaction mixture was evaporated to dryness under reduced pressure, and the residue was dissolved in water (3 ml) and placed in dialysis tubing (MW cut-off 12,000) and dialysed against water (500 ml, pH 6) for 24 hours. The solution was freeze-dried to give the GG167- containing polyacrylamide (5c) as a white solid (5 mg). The $^1$H nmr spectrum (300 MHz) showed the following broad signals: ($D_2O$) δ5.7, 4.4–4.6, 4.1, 3.3–3.7, 3.0, 2.0–2.5, 1.9, 1.1–1.8. By comparison of the integral for the sialic acid protons (δ5.7–3.2) with the integral for the polymer and spacer chains (δ1.0–3.2, minus the N-Acetyl peak at 1.9) the level of incorporation of GG167 units was estimated to be about 10%.

EXAMPLE 7

Preparation of Polyacrylamide 51 which Has Both GG167 Ligands and Biotin Ligands A solution of pNAS (170 mg, 1 mmol of NAS) (MW about 50,000) in DMF (3 ml) was stirred at room temperature, and a solution of compound 2a (TFA salt, 30 mg, 50 μmol) and N-6-aminohexyl-biotinamide (7 mg, 20 μmol) in DMF (2 ml) was added. Triethylamine (50 μl) was added and the reaction mixture was stirred at 20° for 24 hours. Dilute ammonia (20 ml, 5%) was added to the reaction mixture and stirring continued for another 24 hours. The reaction mixture was evaporated to dryness and the residue was dissolved in 10 ml of water and dialysed in water for 2 days (1×4 liters, tubing of 12,000 MW cut-off). With the Sakaguchi guanidine colour test a positive result was obtained from the fluid remaining in the tubing, but not from a concentrated sample of the last dialysis water. The liquid from the dialysis tubing was freeze-dried to give 51 as a cream fluffy solid (71 mg). The level of the ligends on the polymer was estimated by NMR integration, and was consistent with almost complete incorporation of the starting amines.

EXAMPLE 8

Preparation of GG167-Containing Polyacrylamides 5i, 5k, 5m and 5n

Compounds 5i, 5k, 5m and 5n were each prepared by reacting pNAS with the appropriate mixture of GG167 derivative (2a or 2c) and either benzylamine, N-6-aminohexyl-fluorescein or aminoethanethiol, following a similar procedure to that described in Example 7. For the preparation of compounds 5i and 5k (and also compounds 5h and 5j) pNAS of higher MW(>200 Kd) was used.

EXAMPLE 9

Preparation of Dextran (MW 500 KDa) with Multiple GG167 (7-oxycarbamoylhexylamino-carbonyloxy-4-guanidino-Neu5Ac2en) (3.5 mole %) and N-benzylcarbamoyloxy (16.8 mole %) Substituents

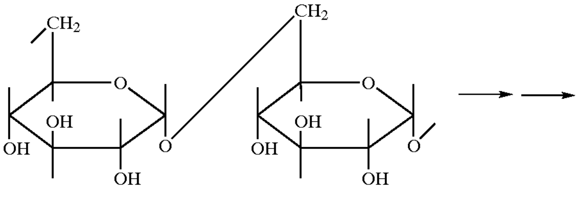

-continued

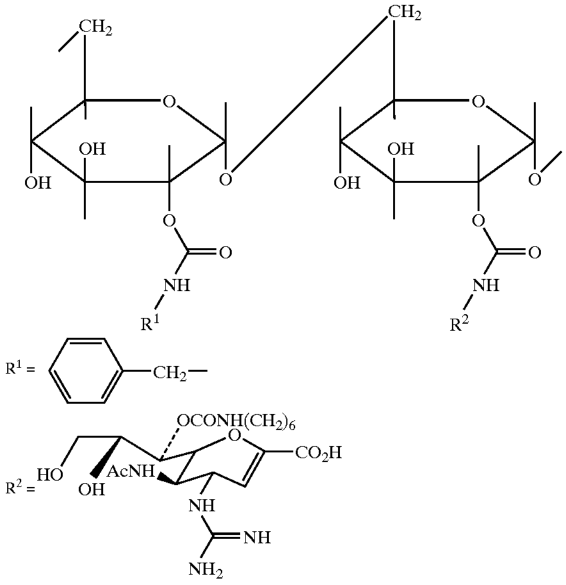

To a solution of Dextran (MW 500,000) [100 mg, 0.617 mmol (based on a unit MW of 162)] in DMSO (5 ml) were added p-nitrophenyl chloroformate (510 mg, 2.53 mmol) and 4-dimethylaminopyridine (309 mg, 2.53 mmol). The mixture was stirred under argon, firstly at room temperature for 1 hr, then at 35~40° C. for 3 hr. The resulting solution was combined with a solution of benzylamine (12.5 mg, 0.117 mmol) and 4-dimethylaminopyridine (40 mg, 0.327 mmol) in pyridine (5 ml). The reaction mixture was allowed to agitate under argon at room temperature for 16 hrs. before being evaporated under high vacuum to dryness. The residue was stirred in 2% potassium carbonate solution (25 ml) at 50° C. for 3 hrs. to produce a clear solution, which was then adjusted to pH7 with 3M HCl. The resulting solution was dialyzed against water at room temperature for 3 days, freeze-dried to afford benzylated dextran (95 mg, 83.4%) as a white solid containing 16.8 mole % of oxycarbamoylmethylenebenzene indicated by [1]H-nmr ($D_2O$)

To a solution of the benzylated dextran (5 mg, 0.027 mmol) in DMSO (0.25 ml) were added p-nitrophenyl chloroformate (12.8 mg, 0.063 mmol) and 4-dimethylaminopyridine (7.8 mg, 0.063mmol). The solution was stirred under argon at room temperature for 1 hr, then at 35~40° C. for 3 hrs. Afterwards it was combined with a solution of compound 2a (0.5 mg, 0.00105 mmol) in a mixture of pyridine (0.25 ml) and DMSO (0.25 ml). The reaction mixture was stirred at room temperature for 16 hr before evaporation under high vacuum to dryness. The residue was stirred vigorously in 1% potassium carbonate solution (5 ml) for 4.5 hr to produce a clear solution. It was then adjusted to pH7.5 with 3M HCl, dialysed against water at room temperature for 24 hr and finally lyophilized to afford the title polymer (4.5 mg, 82%) as a white solid. [1]H-nmr ($D_2O$) indicated that the polymer bore 16.8 molecules of benzylamine and 3.5 molecules of compound 2a per 100 glucose units of the carrier. The MW of the polymer was estimated as 623 KDa, and the average MW for one unit of 7-aminohexylaminocarbonyloxy-4-guanidino-Neu5Ac2en was 5770.

EXAMPLE 10

Preparation of Multivalent GG167 (7-oxyacetamidohexylaminocarbonyloxy-4-guanidino-Neu5Ac2en) (3 mole %), N-benzylacetamido-2-oxy (17 mole%) and 2-oxyacetate (20%) on Dextran/5000 KDa

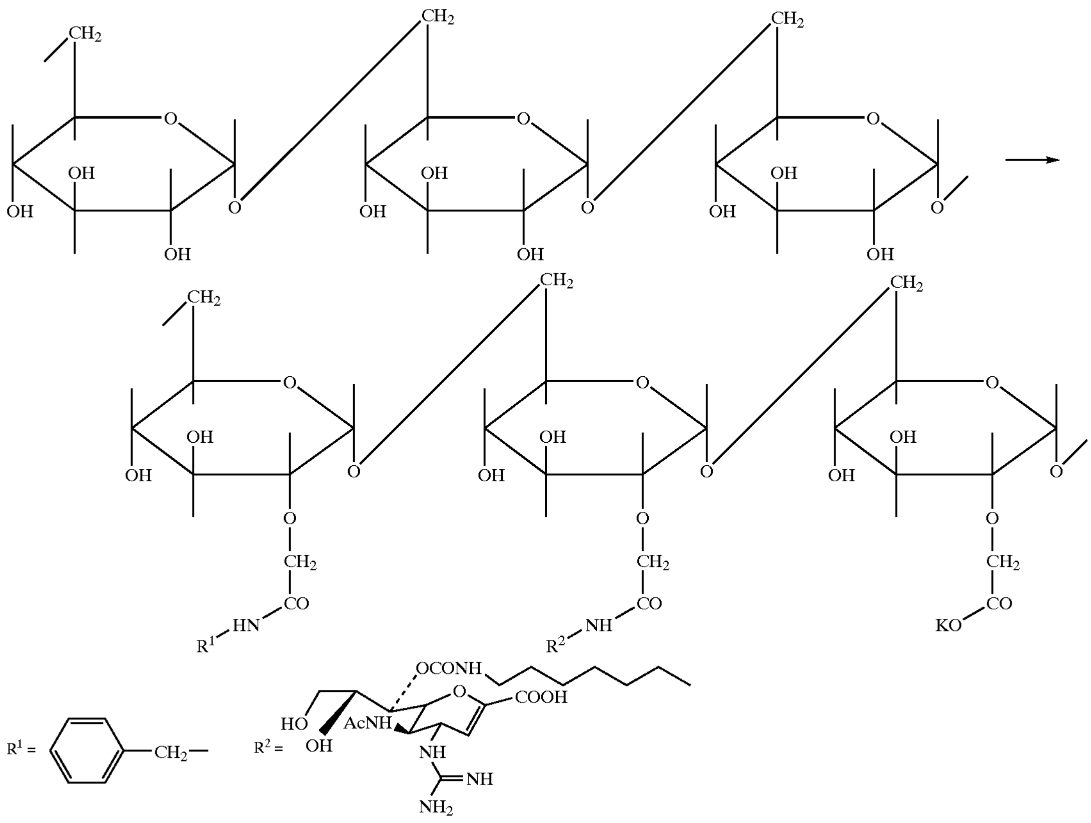

To a solution of Dextran (MW 500,000) [50 mg, 0.308 mmol (based on a unit MW of 162)] in water (0.3 ml) in an ice-bath was added potassium hydroxide (138 mg, 2.46 mmol) in water (0.1 ml). The mixture was stirred at 0~5° C. for 20 min. and then chloroacetic acid (102 mg, 1.07 mmol) was added. The resulting mixture was stirred at 70~80° C. for 20 min. and then at room temperature for 2 hr. The reaction mixture was diluted with methanol (25 ml), the white precipitate collected by filtration, washed thoroughly with fresh methanol (25 ml) and dried. The whole procedure was repeated once to afford product as a white solid containing about 40 mole % of oxyacetate potassium salt as determined by titration (52 mg, 84%).

To a solution of the acetic acid polymer (10 mg, 0.05 mmol) in water (0.4 ml) were added 1-ethyl-3-(3-dimethylaminopropyl)carbodiimide hydrochloride (16 mg, 0.08 mmol) and sulfo-N-hydroxysuccinimide (17.4 mg, 0.08 mmol). The mixture was stirred at room temperature for 20 min. and then combined with a solution of benzylamine (12.8 mg, 0.118 mmol),in methanol (0.2 ml). The resulting mixture was stirred at room temperature for 3 hr and concentrated under vacuum to dryness. The residue was stirred in water (10 ml) containing $NaHCO_3$ (50 mg) at 50° C. to produce a clear solution, which was dialyzed against water for 3 days, lyophilized to afford product (9 mg, 86%) as a white solid containing 17 mole % oxyacetamidomethlenebenzene as indicated by $^1$H-nmr.

To a solution of the polymer (5 mg, 0.0239 mmol) in water (0.2 ml) were added 1-ethyl-3-(3-dimethylaminopropyl)carbodiimide hydrochloride (8 mg, 0.04 mmol) and sulfo-N-hydroxysuccinimide (8.7 mg, 0.04 mmol). The mixture was stirred at room temperature for 20 min., then combined with a solution of compound 2a (1 mg, 0.0021 mmol) and 4-dimethylaminopyridine (3 mg, 0.024 mmol) in pyridine (0.1 ml). The reaction mixture was agitated at room temperature for 3 hr and evaporated to dryness. The residue was stirred in 1% $NaHCO_3$ solution (5 ml) to produce a clear solution. After dialysis in water for 24 hr, the solution was lyophilized to afford the title polymer as a white solid (4.5 g, 84%).

The acid titration and $^1$H-nmr ($D_2O$) indicated that the polymer bore 17 mole % of benzylamine, 3 mole % of GG167 (7-aminohexylaminocarbonyloxy-4-guanidino-Neu5Ac2en) and 20 mole % of acetate per 100 glucose units of the carrier. The MW of the polymer was estimated as 683 KDa and the average MW for one polymeric 7-amino-hexylamino-carbonyloxy-4-guanidino-Neu5Ac2en was 7420.

EXAMPLE 11

Preparation of polymeric-multivalent 7-{6'-{6"-[6'"-(6""-(6'""-aminocaproyl)-aminocaproyl)-aminocaproyl]-aminocaproyl}-aminohexyl}-carbamoyloxy-4-guanidino-Neu5Ac2en (14 mole %) on Oxidized Dextran/500 KDa To a solution of Dextran (MW 500,000) [20 mg, 0.123 mmol (based on a unit MW of 162)] in water (0.4 ml) at ice-bath temperature was added dropwise sodium periodate (15.6 mg, 0.073 mmol) in water (0.4 ml). The reaction mixture was stirred at 5° C. for 2 hr, then allowed to stir at room temperature for 2 hr. The resulting mixture was diluted with water (1.2 ml) and passed through a Sephadex G-25 (10 ml) column. The column was eluted with water (3 ml). The eluate was freeze-dried to afford partially oxidized Dextran (18 mg, 90%) as a white solid.

To a solution of the above oxidised Dextran (3 mg, 0.018 mmol) in water (0.6 ml) were added sodium bicarbonate (15 mg, 0.178 mmol) and compound 2c.TFA salt (6 mg, 0.0057 mmol). The whole mixture was stirred at room temperature for 1 hr, then stirred in an ice-bath temperature. To this cold mixture was added sodium cyanoborohydride (100 mg, 1.59 mmol) in portions. The reaction mixture was stirred at ice-bath temperature for 1 hr, left at 5° C. for 16 hr, then was treated with more sodium cyanoborohydride (100 mg, 1.59 mmol) and stirred at 5° C. for 1 hr, then at room temperature for 2 hr, and finally dialysed against water for 24 hr and lyophilized to give the title polymer (3 mg) as a white solid.

$^1$H-nmr ($D_2O$) indicated that the polymer bore about 430 molecules of 7-{6'-{6"-[6"'-(6""-(6'""-aminocaproyl)-aminocaproyl)-aminocaproyl]-aminocaproyl}-aminohexyl-carbamoyl-oxy-4-guanidino-Neu5Ac2en (compound 2c) per partially oxidized Dextran molecule. Therefore the MW of the polymer was estimated to be 860 KDa and the average MW for each unit of 4-guanidino-Neu5Ac2en was 2,000.

EXAMPLE 12

Preparation of Polymeric-multivalent 7-suberamoyl-hexyl-carbamoyloxy-4-guanidino-Neu5Ac2en (5 mole %) on Polylysine/70~150 KDa A solution of 7-aminohexyl-carbamoyloxy-4-guanidino-Neu5Ac2en (compound 2a, 6.4 mg, 0.0135 mmol) and disuccinimidyl suberate (5 mg, 0.0135 mmol) in a mixture of pyridine (0.1 ml) and DMF (0.1 ml) was stirred at 30° C. for 3 hr, then evaporated to dryness under high vacuum. The residue was taken up in ether (10 ml×3) and dried to afford the activated ester. This was then combined with a solution of polylysine HBr salt (MW70,000–150,000) (10 mg, 0.0485 mmol) in a mixture of water (0.4 ml), DMSO (0.25 ml), DMF (0.6 ml), and pyridine (0.4 ml). The resulting mixture was stirred at room temperature for 10 hr, then dialyzed against water for 72 hr. The dialysate was diluted with water (10 ml), heated to 50° C., before filtration. The filtrate was then lyophilized to afford the title polymer (5 mg) as a white solid.

$^1$H-nmr ($D_2O$) indicated that the polymer bore 5 molecules of 7-suberamoyl-hexylcarbamoyloxy-4-guanidino-Neu5Ac2en per 100 lysine units of the carrier. Therefore the average MW for one polymeric 4-guanidcino-Neu5Ac2en was 5140.

EXAMPLE 13

Preparation of Polymeric-multivalent 7-{2'-[2"-(2"'-aminoethoxy)-ethoxy]-ethyl}-carbamoyloxy-4-guanidino-Neu5Ac2en (3.2 mole %) on Polyglutamic Acid/50~100 KDa To a solution of poly-glutamic acid sodium salt (MW50,000~100,000) (10 mg, 0.0657nnol) in water (0.6 ml) were added 1-(3-dimethylaminopropyl)-3-ethylcarbodiimide hydrochloride (9.6 mg, 0.050 mmol) and N-hydroxysulfo-succinimide (10.9 mg, 0.050 mmol). The mixture was stirred at room temperature for 25 min., then combined with a solution of 7-{2'-[2"-(2"'-aminoethoxy)-ethoxy]-ethyl}-carbamoyloxy-4-guanidino-Neu5Ac2en.TFA salt (compound 2d, 4.1 mg, 0.0081 mmol) in water (0.1 ml) and pyridine (0.1 ml). The resulting mixture was stirred at room temperature for 2 hr. then dialyzed against water for 3 days, and finally lyophilized to afford the title polymer (9.5 mg) as a white solid.

$^1$H-nmr ($D_2O$) indicated that the polymer bore 3.2 molecules of 7-{2'-[2"-(2"'-aminoethoxy)-ethoxy]-ethyl}-carbamoyloxy-4-guanidino-Neu5Ac2en per 100 glutamic acid units of the carrier. The average MW for one polymeric 4-guanidino-Neu5Ac2en was 5250.

EXAMPLE 14

Preparation of N-hydroxyethylpolyacrylamide Conjugated with Compound 2c and Horseradish Peroxidase Compound (2c)TFA salt (6 mg, 0.0057 mmol) was added to a solution of pNAS (see Example 6, part b) (20 mg, 0.118 mmol of NAS) in DMF (1 ml). Triethylamine (20 μl) was added to the clear solution which was stirred at room temperature for 3 days. Half of the above reaction mixture was added to a solution of horseradish peroxidase (17 mg) in water (4 ml) and the mixture was left at 4° C. for several days. Ethanolamine (0.5 ml of a 10% solution in water) was added to the mixture to quench the remaining polyacrylate activated ester. After 2 hr the reaction mixture was dialysed against water for 3 days and then the dialysate was freeze-dried to give the polymeric conjugate as a fluffy pale-brown powder.

EXAMPLE 15

Determination of the Binding of the Compounds of the Invention to Influenza Virus Neuraminidase Two influenza A viruses and one influenza B virus were used to test the ability of the compounds to bind to whole virus influenza neuraminidase. The influenza A reassortants were either A/NWS/34-tern/Australia/G70C/75(H1N9) or A/NWS/Tokyo/3/67/H1N2 and the influenza B strain was B/Victoria/02/87. The neuraminidase assay was carried out following a literature procedure (Potier, M., et al, Anal. Biochem., 1979 94 287), and the measured inhibition constants ($IC_{50}$) are summarised in Table 6.

The inhibition constants for the macromolecules were calculated based on the molecular weight per unit of attached GG167 derivative, e.g. the polyacrylamide 5c which has a GG167-derived molecule bound to 10% of the acrylamide units was assigned a molecular weight of 1293.

TABLE 6

Binding Constants Against Influenza Virus Neuraminidase for Compounds of the Invention

| Compound No. | NWS/Tokyo | NWS/G70C | B/Vic/02/87 |
|---|---|---|---|
| 3a | $1 \times 10^{-8}$ | $7 \times 10^{-9}$ | $2 \times 10^{-8}$ |
| 3b | $2 \times 10^{-9}$ | $2 \times 10^{-9}$ | — |
| 3d | $1 \times 10^{-8}$ | $1 \times 10^{-8}$ | — |
| 4a | $1 \times 10^{-8}$ | $9 \times 10^{-9}$ | $2 \times 10^{-8}$ |
| 4b | $5 \times 10^{-8}$ | $3 \times 10^{-8}$ | $1 \times 10^{-7}$ |
| 4c | $1 \times 10^{-7}$ | $7 \times 10^{-8}$ | — |
| 4d | $1 \times 10^{-7}$ | $1 \times 10^{-7}$ | — |
| 5a | $3 \times 10^{-8}$ | $3 \times 10^{-8}$ | — |
| 5b | $1 \times 10^{-8}$ | $2 \times 10^{-8}$ | — |
| 5c | $1 \times 10^{-8}$ | $2 \times 10^{-8}$ | — |
| 5d | $4 \times 10^{-8}$ | $4 \times 10^{-8}$ | — |

TABLE 6-continued

| Binding Constants Against Influenza Virus Neuraminidase for Compounds of the Invention | | | |
|---|---|---|---|
| Compound No. | NWS/Tokyo | NWS/G70C | B/Vic/02/87 |
| 5e | $2 \times 10^{-8}$ | $3 \times 10^{-8}$ | — |
| GG167 (I) | $1 \times 10^{-9}$ | $1 \times 10^{-9}$ | $1 \times 10^{-8}$ |
| DANA | $6 \times 10^{-6}$ | $6 \times 10^{-6}$ | — |

EXAMPLE 16

Detection of Influenza Virus on ELISA Plates Using Compound No. 4d

A virus solution (50 $\mu$l) of approximately $1\times10^8$ pfu/ml of NWS/G70C influenza A virus in phosphate-buffered saline (PBS) was added directly into the wells of a 96-well ELISA (Dynatech) plate, and the virus was allowed to bind by standing overnight at 4° C. After washing, the plates were blocked with PBS-Tween 20 according to standard procedures, and then serial dilutions of Compound No. 4d were added to one of the ELISA plate rows, starting at 1 $\mu$M concentration of GG167 units and going down to $10^{-10}$ M. As a control, serial dilutions of a biotinylated monoclonal anti-neuraminidase NC10 antibody (L. C. Gruen, J. Immunological Methods, 1994 168 91) were added to another row of the ELISA plate. After incubation for 1 hour the plates were washed to remove unbound compound, and then the virus was detected with Streptavidin-HRPO (Boehringer-Mannheim), using ABTS (Sigma) as the chromogenic substrate and about thirty minutes incubation.

Concentrations of Compound No. 4d above $10^{-9}$ M allowed detection of the virus, and an increasingly strong signal was observed, in parallel with increasing compound concentration. Thus the approximately $5\times10^6$ virus particles per well could readily be detected with Compound No. 4d. The biotinylated antibody control gave a similar level of signal.

EXAMPLE 17

Capture and Detection of a Complex between Influenza Virus and Compound No. 3a

To allow coating of virus particles with the GG167-biotin derivative, 10 $\mu$l of a solution of the NWS/G70C influenza A virus ($1\times10^8$ pfu/ml) was pre-incubated for 1 hour with various concentrations of compound 3a in the wells of separate rows of an ELISA plate. Half $\log_{10}$ dilutions of compound No. 3a were used, starting from 1 $\mu$M concentration of GG167 units and going down to 0.00001 $\mu$M. The virus-compound complexes were then transferred to an ELISA plate which had been pre-coated with avidin and incubated for 1 hour to allow capture. The plates were washed in PBS-Tween 20, and the captured virus was detected with a polyclonal rabbit antibody directed to the virus hefagglutinin according to standard procedures.

The best result was found with a 0.1 $\mu$M concentration of Compound No. 3a, which clearly allowed detection of virus at $10^6$ pfu. At higher concentrations of compound the signal was weaker, possibly due to the blocking of some avidin sites by free compound No. 3a, whilst at lower concentrations (<0.001 $\mu$M) the detection signal was also weaker, probably due to there being insufficient compound to bind fully to all of the virus particles.

EXAMPLE 18

Direct Detection of Influenza Virus-GG167-protein-biotin Conjugate with Streptavidin-Horseradish Peroxidase Following the same procedure as described in Example 17 above and using compound 4d, the direct detection of bound virus with streptavidin-horseradish peroxidase, instead of the anti-hemagglutinin antibody, was also observed.

EXAMPLE 19

Inhibition of Influenza Hemagglutination by Macromolecules of the Invention

Compounds of the invention were tested for the ability to inhibit hemagglutination (HAI) of influenza strains X-31 (H3N2), G70C and Tokyo A, following the standard type of method that has been described in the literature (see for example J. Amer. Chem. Soc., 1997 119 4103 and references cited therein). The HAI assay was performed using solutions of the polymeric GG167 conjugates in PBS which were 2-fold serially diluted across 12 microtitre plate wells. Suspension of virus, diluted to 4 HA units in PBS were added to the wells. After 2 hours at 4° C. 0.5% suspension of chicken erythrocytes was added to each well. After 1 hours at 4° C., the lowest concentration of inhibitor that prevented agglutination of the erythrocytes was determined. The results are summarised in Table 7.

TABLE 7

| | Lowest Concentration ($\mu$M of GG167 units) that Inhibited Agglutination | | |
|---|---|---|---|
| Compound No. | G70C | TOKYO | X-31 |
| Polyacrylamide (assumed Mw 20,000 unsubstituted) | 187.5 | 187.5 | 93.75 |
| 5f | 7.8 | 7.8 | 7.8 |
| 5g | 11.7 | 31.25 | 23.4 |
| 6c | 2.93 | — | 3. 91 |
| Fetuin (control) | 0.73 | 5.86 | <0.48 |

EXAMPLE 20

Inhibition of Influenza Virus Replication by Macromolecules of the Invention

Compounds of the invention were tested for the ability to inhibit the replication of influenza A virus following the standard method that has been described in the literature (see for example Watanabe et al, J. Virological Methods, 1994, 48, 257). The assay was carried out using MDCK cells, and the results are shown in Table 8 below. The results are shown as the minimum compound concentration that inhibits cytopathic effect by 50% [$ID_{50}$ ($\mu$g/ml)], calculated by using a regression analysis program for semilog curve fitting. The results show that all of the macromolecules which have GG167 derivatives attached to them are more active against influenza virus than the unsubstituted backbones by themselves. The results also show that many of the polymeric compounds are more active than the simple monomeric ligand (compound 2c), particularly when calculated on the basis of the molar concentration of GG167 units. The Therapeutic Index for each compound was calculated by dividing the minimum cytotoxic drug concentration (MTC) by the $ID_{50}$.

TABLE 8

| Compound (Molecular weight per GG167 unit) | $ID_{50}$ ($\mu$g/ml) | MTC | Therapeutic Index |
|---|---|---|---|
| GG167 (332) | <0.32 | >100 | >312.5 |
| 2c (1,040) | 3.0 | >100 | >32.8 |
| 3d (10,000) | 1.24 | >100 | >80.9 |
| 5a (1,451) | <0.32 | >100 | >312.5 |
| 5g (2,400) | 1.48 | >100 | >67.4 |
| 5h (4,500) | 1.22 | >100 | >81.8 |
| 5i (5,000) | 1.11 | >100 | >89.6 |
| 5j (4,000) | 3.20 | >100 | >31.2 |
| 5k (4,500) | 0.46 | >100 | >215.6 |
| Polyacrylamide (unsubstituted) | 94.7 | >100 | >1.06 |
| 6a (5,770) | 26.7 | >100 | >3.75 |
| 6c (5,700) | 0.31 | >100 | >322.3 |
| 6d (6,800) | 3.00 | >100 | 33.3 |
| 6e (8,480) | 21.9 | >100 | 4.56 |
| 6f (7,270) | 7.2 | >100 | >13.9 |
| 6g (11,750) | 43.6 | >100 | >2.29 |
| 6h (17,850) | 23.6 | >100 | >4.24 |
| 6i (unsubst. benzyldextran) | >100 | >100 | — |
| 6j (unsubst. benzyldextran) | >100 | >100 | — |
| Example 11 (1,980) | <0.32 | >100 | >312.5 |
| Example 12 (5,140) | 0.45 | 100 | 221.1 |
| Example 13 (5,250) | 0.39 | >100 | >258.7 |
| Ribavirin | 1.0–2.6 | >32 | >12.22–31.98 |

It will be apparent to the person skilled in the art that while the invention has been described in some detail for the purpose of clarity and understanding, various modifications and alterations to the embodiments and methods described herein may be made without departing from the scope of the inventive concept disclosed in this specification.

Reference cited herein are listed on the following pages, and are incorporated herein by this reference.

What is claimed is:

1. A macromolecular compound comprising a macromolecule attached to at least one sialic acid derivative via the C-7 position of the sialic acid derivative structure, wherein the sialic acid derivative binds to the active site of influenza virus neuraminidase but is not cleaved by the neuraminidase.

2. A macromolecular, compound according to claim 1, in which the sialic acid derivative is attached to the macromolecule via a spacer or linker group.

3. The macromolecular compound of claim 2, in which the spacer or linker group Y is selected from the group consisting of aminoalkyl groups, (poly)amino acids, linear peptides, oligosaccharides and polysaccharides, polyethylene glycol units, and aminodialkylureas, or any combination of these groups.

4. A macromolecular compound according to claim 1, in which the sialic acid derivative inhibits influenza virus neuraminidase with an inhibition constant ($IC_{50}$) of $10^{-6}$ M or less.

5. A macromolecular compound according to claim 1, in which the sialic acid derivative is compound (I)

Compound (I)

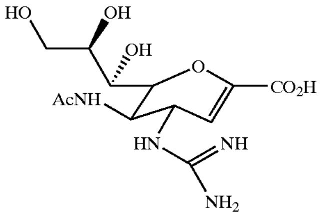

GG167 functionalised via the 7-position of the sialic acid structure.

6. A pharmaceutical composition comprising a compound according to claim 5, together with a pharmaceutically-acceptable carrier, in which the compound has an $ID_{50}$ for neuraminidase of less than 5 $\mu$g/ml.

7. A composition according to claim 6, further comprising one or more additional therapeutically active agents.

8. A composition according to claim 7, in which the additional therapeutically active agent is an anti-viral agent.

9. A method of treating influenza infection in a mammal, the method comprising administering to the mammal the pharmaceutical composition of claim 6.

10. The method of claim 9, wherein the mammal is a human.

11. The macromolecular compound of claim 5, wherein the sialic acid derivative is attached to the macromolecule via a spacer or linker group.

12. The macromolecular compound of claim 11, in which the spacer or linker group is selected from the group consisting of an aminoalkyl group, a (poly)amino acid, a linear peptide, an oligosaccharide, polyethylene glycol, and aminodialkylurea, or any combination of these groups.

13. A method of treating influenza infection in a mammal, the method comprising administering to the mammal an effective amount of the compound of claim 5.

14. The method of claim 13, wherein the mammal is a human.

15. A macromolecular compound according to claim 1 of formula (II):

$$(X—Y)_n—M—(Z)_m \qquad (II)$$

wherein X is a neuraminidase-binding 2,3-dehydro-sialic acid derivative (2);

(2)

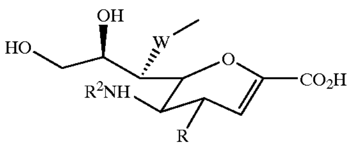

which is linked at the W via a spacer group Y to a macromolecule M, and Z is an optional extra substituent on the macromolecule;

wherein R represents an azido group, an unsubstituted or substituted guanidino group, or an unsubstituted or substituted amino group;

$R^2$ represents $COCH_3$, $COCF_3$, $SO_2CH_3$ or $SO_2CF_3$;

W represents O(C═O)NH, O(C═S)NH, NH(C═O)NH or NH(C═S)NH and is attached through the NH to the spacer group Y;

m is an integer between 0 and 1000;

in is an integer between 1 and 1,000;

the spacer group Y is an optionally substituted chain of up to 1000 atoms chosen from carbon, nitrogen, oxygen and sulphur; and the macromolecule M is a synthetic or natural polymer, protein, antibody or enzyme of molecular weight from $10^4$ up to $10^7$, linked covalently or non-covalently to the spacer group Y.

16. A macromolecular compound according to claim 15, in which Z is present and is a group which binds hemagglutinin.

17. A macromolecular compound according to claim 15, in which the spacer group Y is selected from the group consisting of aminoalkyl groups, (poly)amino acids, linear peptides, oligosaccharides and polysaccharides, polyethylene glycol units, and aminodialkylureas, or any combination of these groups.

18. A macromolecular compound according to claim 17, in which the spacer group Y has a terminal amino-group.

19. A macromolecular compound according to claim 17, in which all spacer groups Y in the compound are identical.

20. A macromolecular compound according to claim 17, in which the spacer groups Y are a combination of moieties selected from the group consisting of aminoalkyl groups, (poly)amino acids, linear peptides, oligosaccharides, polysaccharides, polyethylene glycol units, and aminodialkylureas.

21. A macromolecular compound according to claim 15, in which the macromolecule M is selected from the group consisting of proteins, enzymes, antibodies, water-soluble synthetic polymers, polysaccharides and polyaminoacids.

22. A macromolecular compound according to claim 15, in which the macromolecule M is selected from the group consisting of bovine serum albumin, horseradish peroxidase (HRP), avidin, streptavidin, neutravidin, and immunoglobulins.

23. A macromolecular compound according to claim 15, in which the macromolecule M is selected from the group consisting of polysaccharides, polyacrylamides, polyethylene glycols, polyureas, polyacids, polyesters, polyamides and N-(2 hydroxypropyl)methacrylamide (HMPA), said macromolecule being pharmaceutically acceptable.

24. A macromolecular compound according to claim 15, in which R is a guanidino or amino group substituted with a methyl, ethyl, allyl, amino, cyano or nitro group.

25. A macromolecular compound according to claim 15, in which X is a compound of formula (2), in which R is guanidine, $R^2$ is acetyl, W is the group O(=CO)NH, and the spacer group Y is a chain made up of between 6 and 60 carbon, nitrogen and oxygen atoms.

26. A pharmaceutical composition comprising a compound according to claim 15 together with a pharmaceutically-acceptable carrier, in which the compound has an $ID_{50}$ for influenza virus neuraminidase of less than 5 μg/ml.

27. A composition according to claim 26, further comprising one or more additional therapeutically active agents.

28. A composition according to claim 27, in which the additional therapeutically active agent is an anti-viral agent.

29. A method of treating influenza infection in a mammal, the method comprising administering to the mammal the pharmaceutical composition of claim 26.

30. The method of claim 29, wherein the mammal is a human.

31. A method of treating influenza infection in a mammal, the method comprising administering to the mammal an effective amount of the compound of claim 15.

32. The method of claim 31, wherein the mammal is a human.

33. A pharmaceutical composition comprising a compound according to claim 1, together with a pharmaceutically-acceptable carrier, in which the compound has an $ID_{50}$ for neuraminidase of less than 5 μg/ml.

34. A composition according to claim 33, further comprising one or more additional therapeutically active agents.

35. A composition according to claim 34, in which the additional therapeutically active agent is an anti-viral agent.

36. A method of treating influenza infection in a mammal, the method comprising administering to the mammal the pharmaceutical composition of claim 33.

37. The method of claim 36, wherein the mammal is a human.

38. A method of treating influenza infection in a mammal, the method comprising administering to the mammal an effective amount of a compound according to claim 1.

39. The macromolecular compound of claim 1, in which the macromolecule is selected from the group consisting of a protein, an enzyme, an antibody, a water-soluble synthetic polymer, a polysaccharide and a polyaminoacid.

40. The macromolecular compound of claim 1, in which the macromolecule is selected from the group consisting of bovine serum albumin, horseradish peroxidase (HRP), avidin, streptavidin, neutravidin, and an immunoglobulin.

41. The macromolecular compound of claim 1, in which the macromolecule is as selected from the group consisting of a polysaccharide, a polyacrylamide, a polyethylene glycol, a polyurea, a polyacid, a polyester, a polyamide and N-(2 hydroxypropyl)methacrylamide (HMPA).

* * * * *